(12) United States Patent
Smith et al.

(10) Patent No.: US 11,090,426 B2
(45) Date of Patent: Aug. 17, 2021

(54) AMBULATORY INFUSION PUMP WITH CONFIGURABLE BATTERY COMPARTMENT

(71) Applicant: B. BRAUN MEDICAL INC., Bethlehem, PA (US)

(72) Inventors: Dan Smith, Portsmouth, RI (US); Spencer Brown, Cranston, RI (US); Benjamin Vespone, North Providence, RI (US)

(73) Assignee: B. Braun Medical Inc., Bethlehem, PA (US)

( * ) Notice: Subject to any disclaimer, the term of this patent is extended or adjusted under 35 U.S.C. 154(b) by 167 days.

(21) Appl. No.: 16/689,698

(22) Filed: Nov. 20, 2019

(65) Prior Publication Data

US 2021/0146033 A1 May 20, 2021

(51) Int. Cl.
*A61M 5/142* (2006.01)
*H01M 50/20* (2021.01)
*H01M 50/502* (2021.01)

(52) U.S. Cl.
CPC ............ *A61M 5/142* (2013.01); *H01M 50/20* (2021.01); *H01M 50/502* (2021.01); *A61M 2205/8206* (2013.01); *A61M 2205/8256* (2013.01)

(58) Field of Classification Search
CPC .... A61M 5/14; A61M 5/14244; A61M 5/145; A61M 2205/82; A61M 2205/8237; A61M 2205/8206; A61M 2205/8256; A61M 5/142; H01M 50/20; H01M 50/502
See application file for complete search history.

(56) References Cited

U.S. PATENT DOCUMENTS

| | | | |
|---|---|---|---|
| 2005/0020980 A1* | 1/2005 | Inoue | A61M 39/10 604/152 |
| 2008/0294109 A1* | 11/2008 | Estes | A61M 5/14244 604/141 |
| 2010/0022992 A1* | 1/2010 | Genosar | A61M 5/145 604/891.1 |

* cited by examiner

*Primary Examiner* — Jason E Flick

(57) ABSTRACT

An ambulatory pump and a battery compartment for use in an ambulatory pump. The ambulatory pump includes a pump, a controller coupled to the pump for controlling the pump to deliver fluid to a patient, and a battery compartment electrically coupled to the pump and the controller. The battery compartment defines a cavity for alternately receiving a battery pack and a plurality of household batteries. A flex guide is positioned within the cavity. The flex guide has a compressed state and a non-compressed state where a profile of the flex guide has a height that is greater than half the insertion depth of the household batteries in the non-compressed state and that is less than half the insertion depth in the compressed state.

20 Claims, 8 Drawing Sheets

AMBULATORY INFUSION PUMP WITH CONFIGURABLE BATTERY COMPARTMENT

BACKGROUND

Infusion pumps deliver controlled doses of fluids such as medications, analgesics, and nutrition to patients. Infusion pumps are particularly well suited to delivering controlled doses over long periods of time, e.g., several hours or days. In addition to delivering fluids over long periods of time, an infusion pump can be used to deliver fluids on a timed schedule. The fluids being provided by the infusion pumps are often vital to the patient's stabilization and/or recovery.

While many infusion pumps are designed for bedside use, there are ambulatory versions available. Ambulatory infusion pumps allow a patient to move around while the infusion pump is in use. This can be beneficial for patients who would otherwise be confined to a bed, and it can help patients get some light exercise by walking or stretching. This also allows medications and nutrition to be delivered while patients are being transferred.

Ambulatory infusion pumps require a portable power source in order to continuously deliver the vital medications and nutrition while mobile. Due to the vital nature of the medications and nutrition and the need for their continuous delivery, there is a need for improved power delivery systems.

SUMMARY

Examples described herein are directed to an ambulatory pump and a battery compartment for use in an ambulatory pump. The ambulatory pump includes a pump, a controller coupled to the pump for controlling the pump to deliver fluid to a patient, and a battery compartment electrically coupled to the pump and to the controller. The battery compartment defines a cavity for alternately receiving a battery pack and household batteries. A flex guide is positioned within the cavity and each of the household batteries have an insertion depth. The flex guide has a compressed state and a non-compressed state where a profile of the flex guide has a height that is greater than half the insertion depth in the non-compressed state and that is less than half the insertion depth in the compressed state. In an example, the flex guide constrains the household batteries to a portion of the cavity when in the non-compressed state and enables the battery pack to utilize a larger portion of the cavity when in the compressed state.

DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a small letter may be used to distinguish between the multiple elements. When the multiple elements are referred to collectively or a non-specific one of the multiple elements is being referenced, the small letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1:
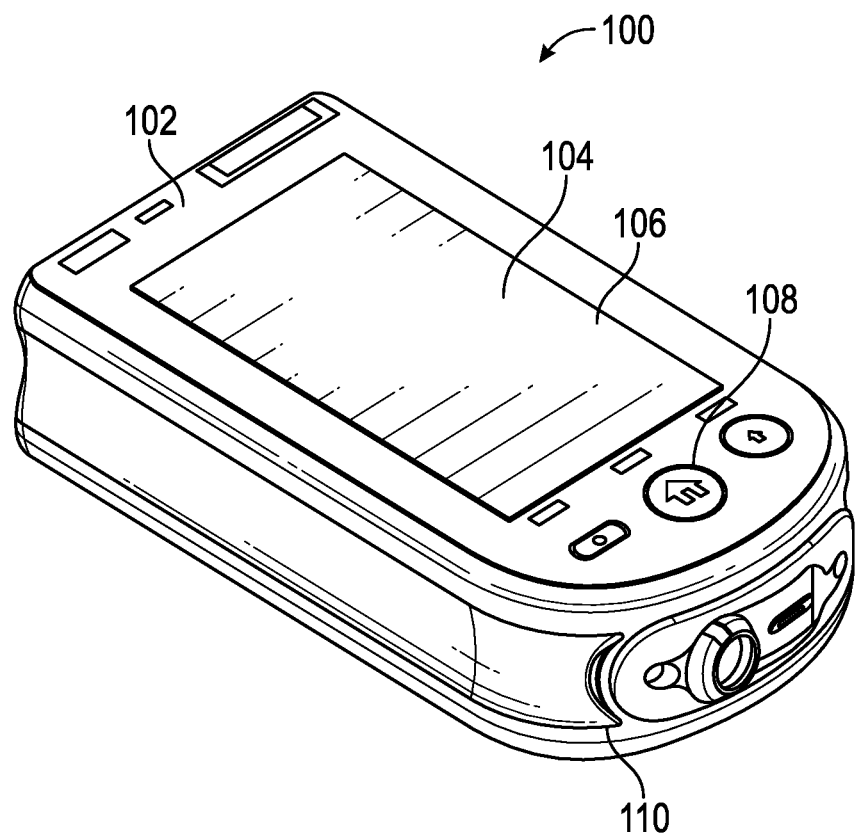
FIG. 1 is a perspective front view of an example ambulatory infusion pump.

FIG. 1 depicts an example ambulatory pump 100. The pump 100 includes a peristaltic pump mechanism (not shown in FIG. 1) for pumping fluid from a fluid container (e.g., a bag or a bottle) into a patient. The pump 100 has a front face 102 that includes a user interface 104 for interacting with the pump 100. The illustrated user interface 104 includes a display 106 (which may be a touchscreen) and buttons 108. A user controls operation of the pump via the user interface 104. The pump 100 additionally includes a housing 110 for containing and supporting the components of the pump 100.

Figure 2:
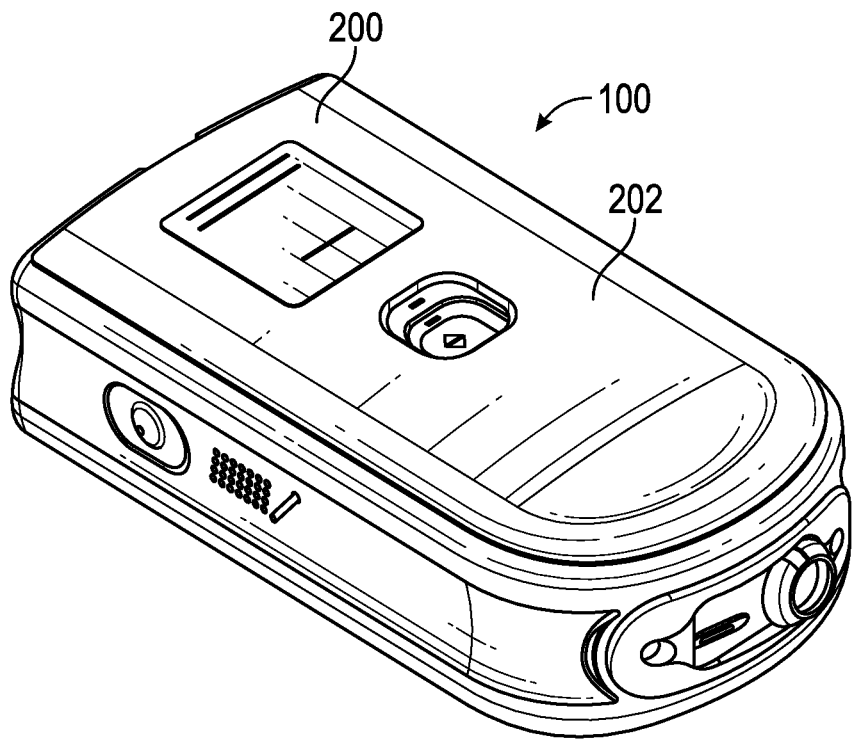
FIG. 2 is a perspective rear view of the example ambulatory infusion pump of FIG. 1.

FIG. 2 depicts a back face 200 of the pump 100. An access cover 202 is positioned on the back face 200 of the pump. Removing the access cover 202 provides access to a battery compartment for receiving alternate power sources (e.g., household batteries and a battery pack), which is described in further detail below.

Figure 3A:
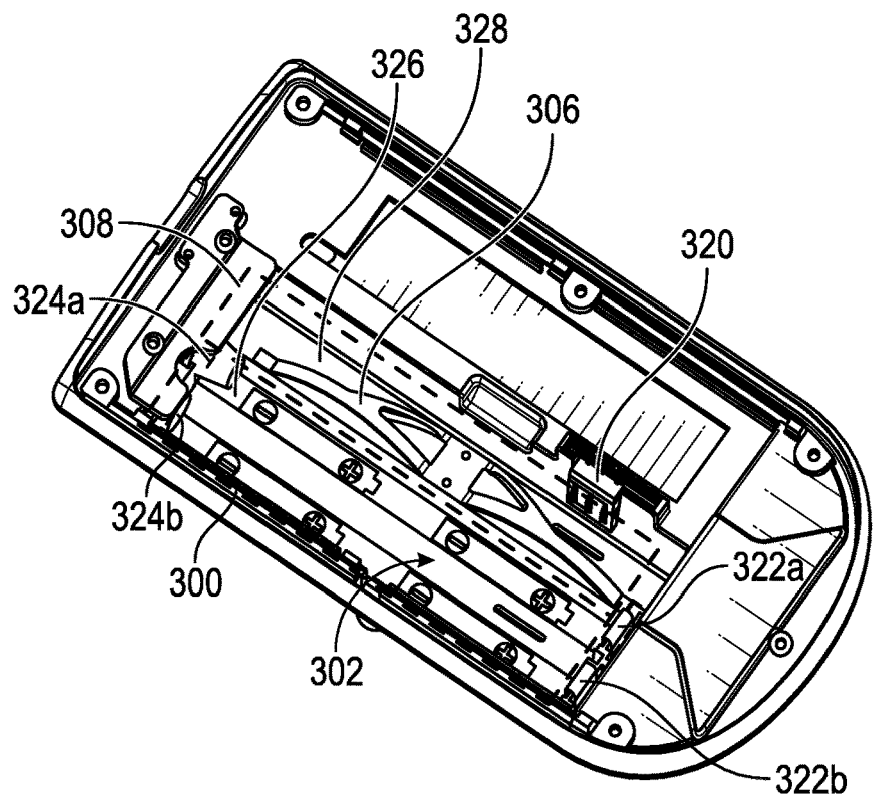
FIG. 3A is a perspective rear view of the example ambulatory infusion pump of FIG. 1 with the back cover removed.

FIG. 3A depicts the back of the pump 100 with the access cover 202 removed to reveal a battery compartment 300. The battery compartment 300 includes a cavity 302 sized to receive alternate power sources. The cavity 302 includes a first portion 326 that is smaller than a second portion 328 (which includes the first portion 326). The first portion 326 is sized to receive household batteries (four AA batteries in the illustrated example). The second portion 328 is sized to receive a battery pack that is larger than the area required for the household batteries. Although the examples are illustrated using AA cylindrical household batteries, other types of household batteries may be used such as AAA, AA, C, D, and 9-volt type batteries. Suitable modifications to the cavity 302, flex guide 306, and electrical connectors 322/324 to accommodate alternative household batteries will be understood by one of skill the art from the description herein.

A flex guide 306 in positioned in the second portion 328 between the first portion 326 and a battery pack connector 320. The flex guide 306 includes a non-compressed state in which the flex guide 306 defines one side of the first portion 326, effectively reducing the size of the cavity 302 to the first portion 326 in order to prevent side to side movement of the household batteries (i.e., a household battery configuration). The flex guide 306 additionally includes a compressed state in which the flex guide 306 is flattened, effectively increasing the size of the cavity 302 to the second portion 328 to allow insertion of the battery pack (i.e., a battery pack configuration). In an example, the cavity is 117 mm in length, 44.5 mm in width, and 18 mm in depth. When the flex guide 306 is in the compressed state, the full width of the cavity 302 is available to receive the battery pack. When the flex guide 306 is in the non-compressed state, the effective width of the cavity 302 is reduced to the width of two household batteries positioned side by side, e.g., approximately 28 mm.

The battery compartment 300 includes a hold-down brace 308 for securing one end of a battery pack during insertion. In use, a battery pack is inserted into the cavity 302 by positioning one end of the battery pack under the hold-down brace 308 (to toe-in the battery pack) and pressing the battery pack down until a mating connector on the battery pack mates with the battery pack connector 320. As the battery pack is pressed down, it compresses the flex guide 306 to effectively expand the cavity 302 and permit full insertion of the battery pack. The hold-down brace 308 may be a separate component or may be integrally formed as part of the cavity 302. Additionally, the hold-down brace 308 may be positioned to protect the connectors 324 during insertion of the batteries or battery pack.

The battery compartment 300 additionally includes electrical connectors for the household batteries. The electrical connectors include a first electrical connector 322a and a second electrical connector 322b on one side of the cavity and a third electrical connector 324a and a fourth electrical connector 324b on an opposite side of the cavity. The first and second electrical connectors 322a and 322b each include a conductive surface that is electrically coupled to electronics within the pump 100. The third and fourth electrical connectors 324a and 324b each include a conductive, spiral compression spring that is also electrically coupled to electronics within the pump 100. When household batteries are installed in the pump 100, the electrical connectors 322/324 both provide electrical connection between the batteries and the electronics of the pump 100 and constrain movement of the batteries in the longitudinal direction. When a battery pack is installed, the electrical connectors 322/324 constrain movement of the battery pack in the longitudinal direction, but do not provide an electrical connection between the battery pack and the electronics of the pump 100. Rather, the connector 320 provides electrical connection between the battery pack and the electronics of the pump 100.

Figure 3B:
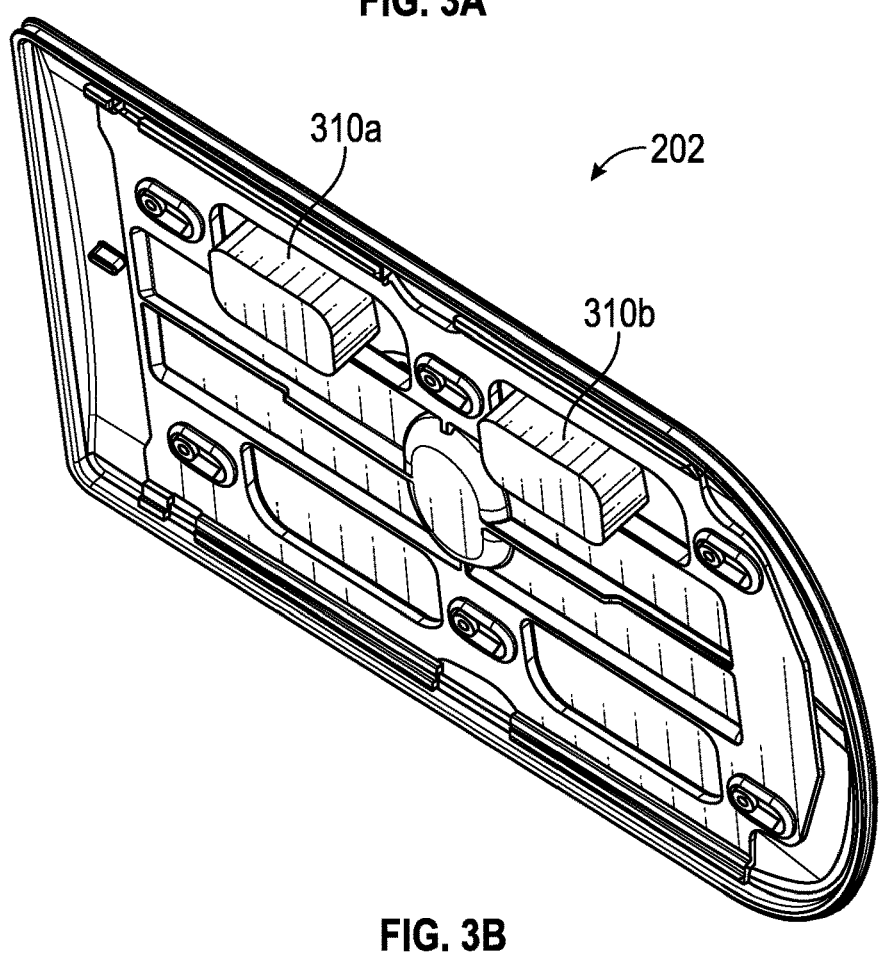
FIG. 3B is a perspective bottom view of the back cover of the example ambulatory infusion pump of FIG. 1.

FIG. 3B depicts an underside of the access cover 202. The underside of the access cover 202 includes a first resilient member 310a and a second resilient member 310b. The resilient members 310 may be foam pads. The resilient members 310 are positioned on the access cover 202 such that, when the access cover 202 is attached to the housing 110, a plane extending perpendicular from a surface of the resilient member 310 facing the batteries extends between latitudinally adjacent batteries (i.e., batteries that are side-by-side).

Figure 4A:
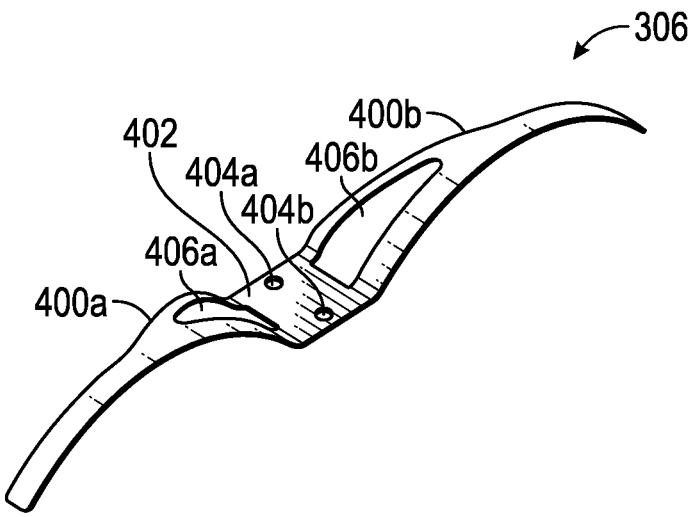
FIG. 4A is a perspective view of the glide spring in an uncompressed state used in the battery compartment of the example ambulatory infusion pump of FIG. 1.

FIG. 4A depicts the flex guide 306. The flex guide 306 includes a first arch 400a and a second arch 400b. The arches 400 are separated by an attachment region 402 configured for attachment to a bottom surface of the battery compartment. The attachment region 402 is attached to the bottom surface via connection points 404a and 404b. The connection points 404a and 404b may be spot welds, screws, or other connection means. The first arch 400a includes a first cutout 406a and the second arch 400b includes a second cutout 406b. The cutouts 406 are sized to tune the rigidity of the arches 400. Although the flex guide 306 is depicted and described as a single unit, it could be separate units (e.g., a separate unit/arch for each battery being constrained). Additionally, although depicted on one side of the battery compartment, flex guides may be positioned on opposite sides of the battery compartment with the batteries constrained therebetween. The flex guide 306 may be made of an elastic material such as spring steel or other material that is compressible under a compression force and returns to its original shape after the compression force is removed.

Figure 4B:
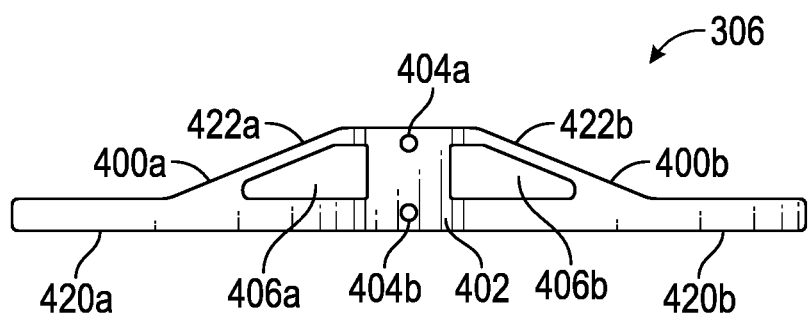
FIG. 4B is a top view of the glide spring of FIG. 4A.

FIG. 4B depicts a top view of the flex guide 306. As can be seen in FIG. 4B, the first arch 400a includes a first edge 420a and the second arch 400b includes a second edge 420b that are in a single plane that is perpendicular to the bottom surface of the battery compartment/cavity when mounted in the battery compartment. The first arch 400a includes a third edge 422a and the second arch 400b includes a fourth edge 422b that are not in a single plane that is perpendicular to the bottom surface of the battery compartment when mounted in the battery compartment.

Figure 4C:
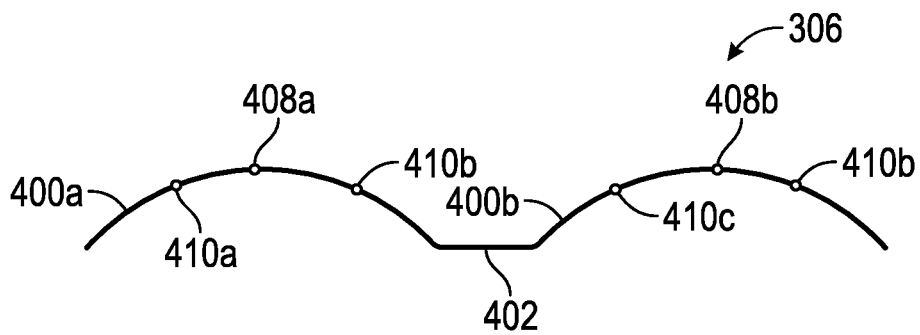
FIG. 4C is a side view of the glide spring of FIG. 4A.

FIG. 4C depicts a side view (profile) of the first edge 420a and 420b of the flex guide 306. The first edge 420a of the first arch 400a includes a first apex 408a, a first touch zone 410a, and a second touch zone 410b. The second edge 420b of the second arch 400b includes a second apex 408b, a third touch zone 410c and a fourth touch zone 410d. In the uncompressed state, the first apex 408a and the second apex 408b each have a height (e.g., 8.7 mm) that is greater than half the insertion depth of an adjacent household battery (i.e., a height that is greater than the radius/midpoint of a cylindrical household battery or the midpoint of a rectangular battery). Each arch 400 may be configured and positioned within the battery compartment such that the respective apex 408 corresponds to the midpoint of the adjacent household battery in the longitudinal direction. As used herein, the insertion depth is in a direction perpendicular to the bottom surface of the battery compartment/cavity configured to receive the batteries.

Having an apex height extending above the radius/midpoint of an adjacent cylindrical household battery enables each arch to contact the adjacent cylindrical battery in two distinct touch zones (e.g., the first touch zone 410a and the second touch zone 410b contact a first cylindrical battery in two distinct regions and the third touch zone 410c and the fourth touch zone 410d contact a second cylindrical battery in two distinct regions). By providing two distinct touch zones for each cylindrical battery, the flex guide 306 reliably provides structural support to prevent movement of the batteries within the cavity. Each of the touch zones may be a point of contact, a line contact, or an area contact (e.g., depending on the material and/or shape of the flex guide 306.

Figure 4D:
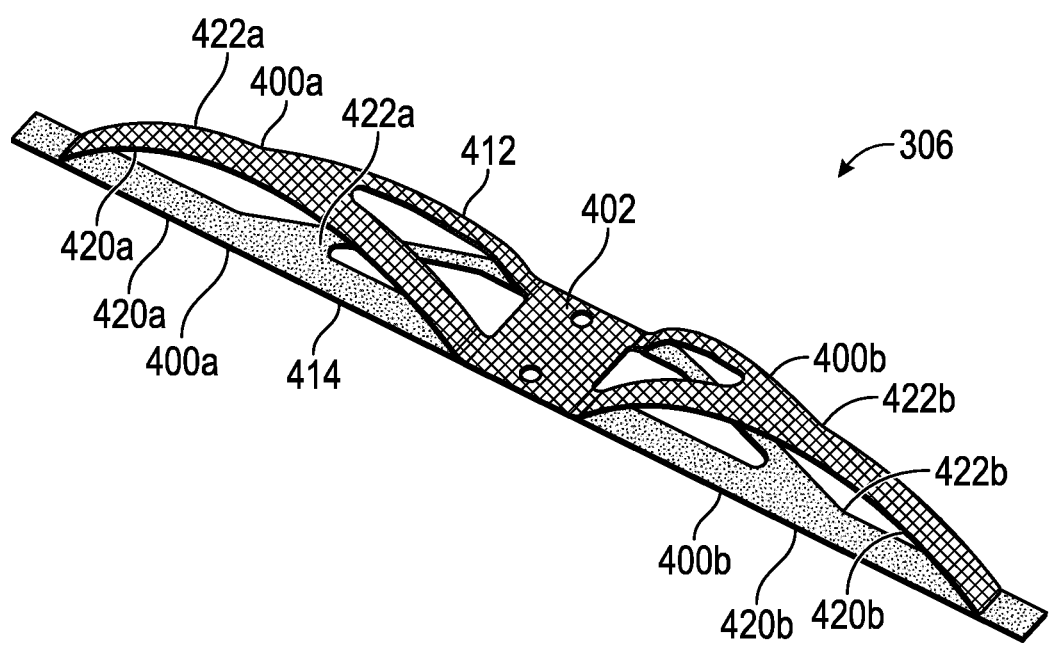
FIG. 4D is a transition view of the glide spring of FIG. 4A in an uncompressed state (household battery configuration) and a compressed state (battery pack configuration).

FIG. 4D depicts the flex guide 306 in both the non-compressed state 412 and the compressed state 414. As can be seen in FIG. 4D, movement of the arches 400 between the non-compressed state 412 and the compressed state 414 results in the first edge 420a and the second edge 420b moving in a single plane that is perpendicular to the bottom of the battery compartment when mounted in the battery compartment. Because of the shape of the third edge 422a and the fourth edge 422b, movement of the arches 400 between the non-compressed state 412 and the compressed state 414 does not result in those edges moving in a single plane that is perpendicular to the bottom of the battery compartment.

Figure 5A:
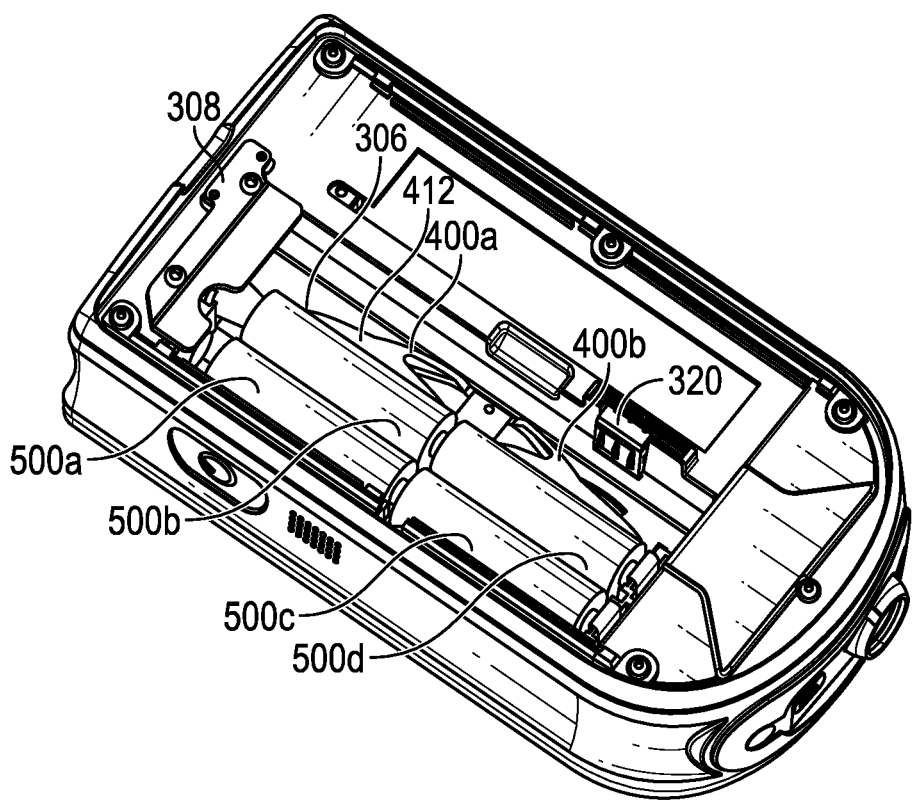
FIG. 5A is a rear perspective view of the example ambulatory infusion pump of FIG. 1 with back cover removed in a household battery configuration with household batteries installed.
Figure 5B:
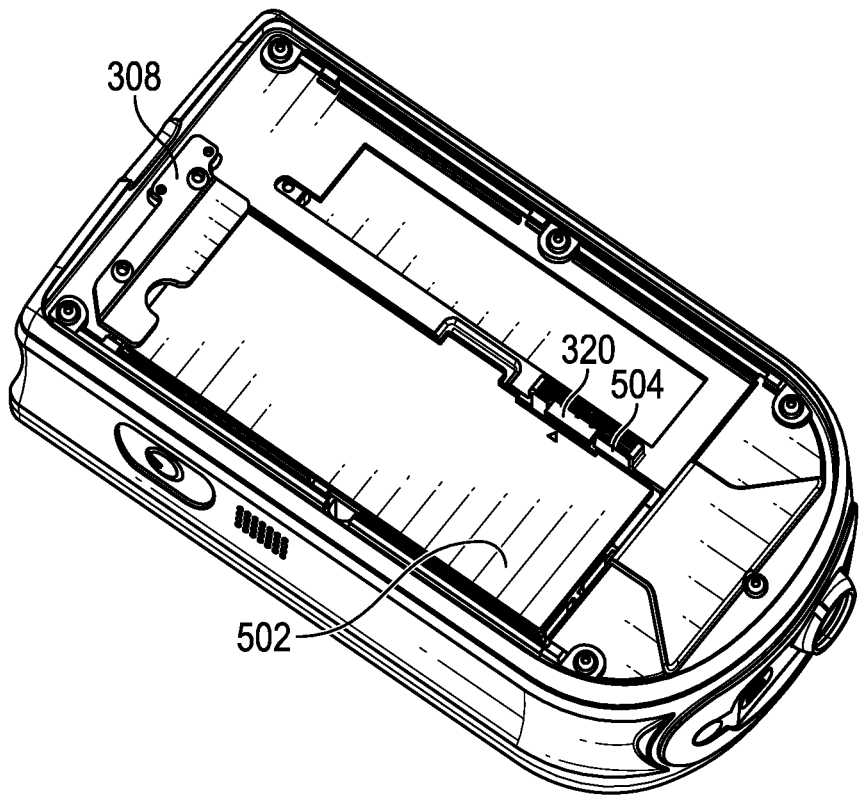
FIG. 5B is a rear perspective view of the example ambulatory infusion pump of FIG. 1 with back cover removed in a battery pack configuration with a battery pack installed.

FIG. 5A depicts the pump 100 with four cylindrical batteries 500a-d installed and FIG. 5B depicts the pump 100 with a battery pack 502 installed. When the cylindrical batteries 500 are installed, the flex guide 306 is in the non-compressed state 412, which laterally constrains the batteries 500 toward one side of the battery compartment. When the battery pack 502 is installed, the flex guide 306 is in the compressed state 414, having been compressed by the insertion of the battery pack 502. This also allows a mating connector 504 of the battery pack 502 to mate with the battery pack electrical connector 320.

Figure 6C:
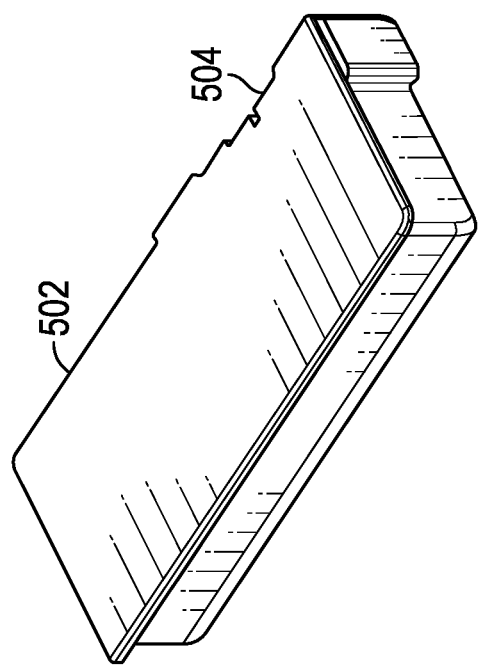
FIG. 6C is a diagram of an example battery pack for insertion in the battery cavity of the example ambulatory infusion pump of FIG. 1.
Figure 6B:
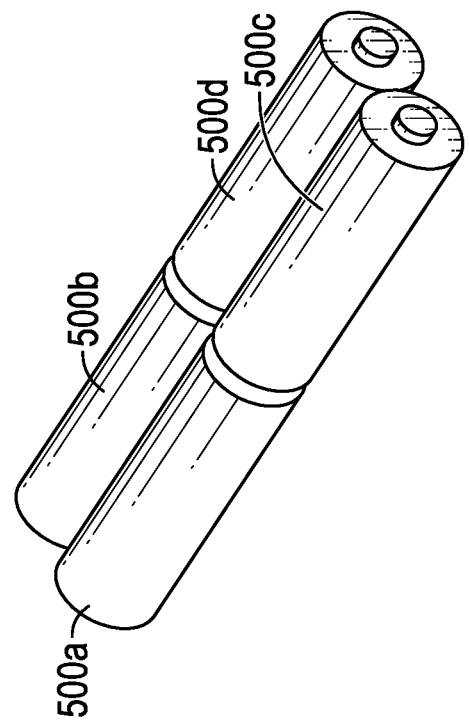
FIG. 6B is a diagram of four cylindrical household batteries in accordance with the prior art for insertion in the battery cavity of the example ambulatory infusion pump of FIG. 1.
Figure 6A:
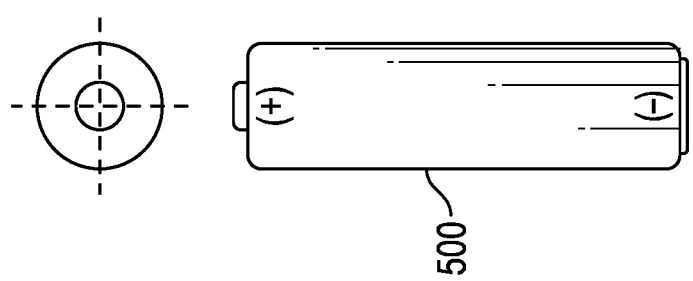
FIG. 6A is a diagram of a cylindrical household battery in accordance with the prior art for insertion in the battery cavity of the example ambulatory infusion pump of FIG. 1.

FIG. 6A depicts a prior art AA cylindrical battery 500. The battery 500 is approximately 50 mm in a longitudinal direction and has a radius of approximately 7 mm. FIG. 6B depicts four batteries 500a-d arranged as they would be for insertion within the first portion 326 of the cavity 302. The batteries 500 are arranged such that there are two adjacent sets of batteries that are connected in series (i.e., a first set including batteries 500a and 500c and a second set including batteries 500b and 500d). This arrangement of batteries fits within a rectangular prism that is 101 mm in length, 28 mm in width, and 14 mm in depth. FIG. 6C depicts an example battery pack 502. The depicted battery pack is a substantially rectangular prism that is 113 mm in length, 43 mm in width, and 15 mm in depth. Rectangular prism dimension differences between the cylindrical household batteries 500 and the battery pack 502 are accommodated by the electrical contacts 322/324 in the longitudinal direction, the flex guide 306 in the lateral direction, and the resilient member(s) 310 in depth.

Figure 7A:
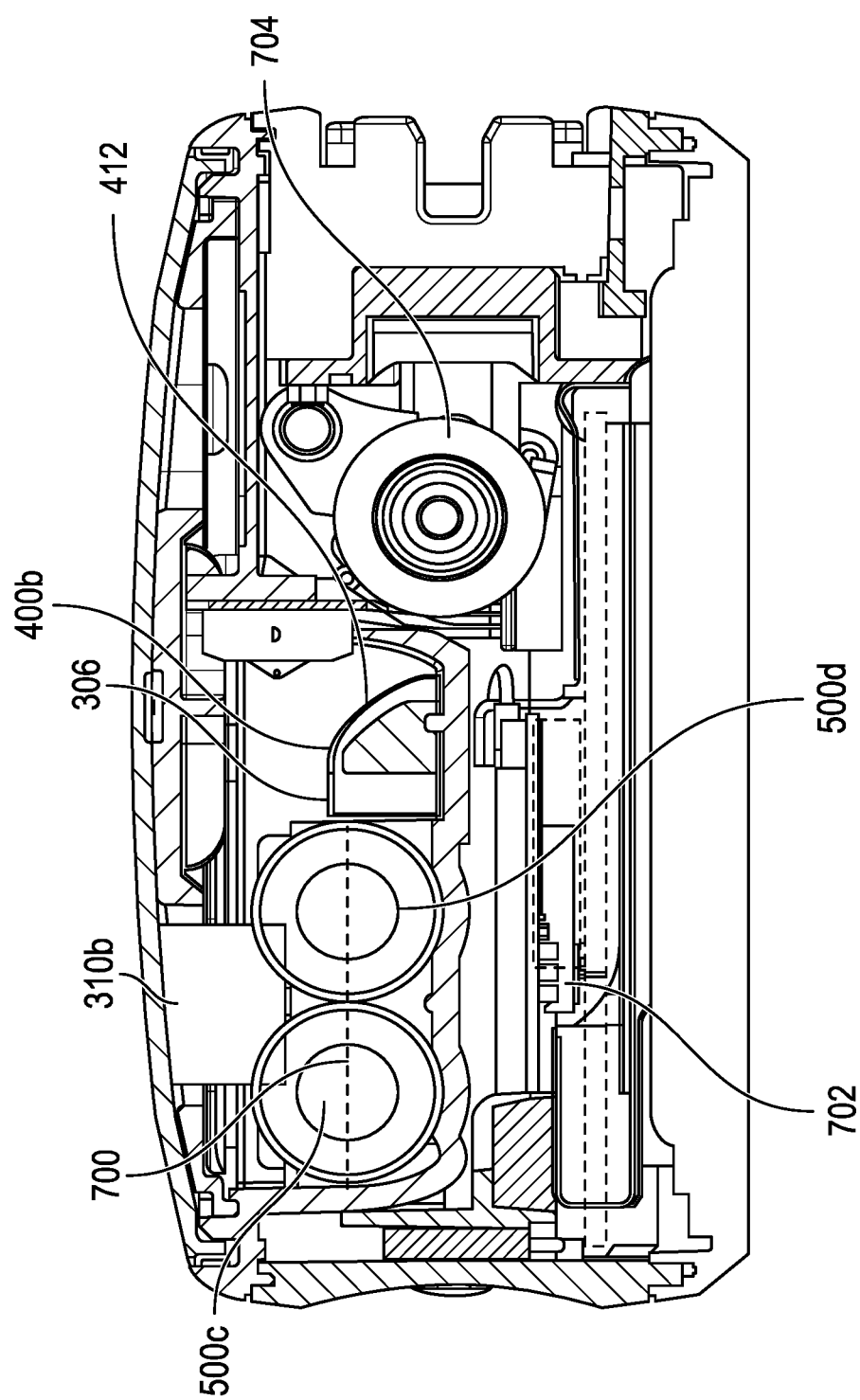
FIG. 7A is a bottom cutaway view of the example ambulatory infusion pump of FIG. 1 in the household battery configuration with the cylindrical household batteries installed.

FIG. 7A depicts a bottom cutaway view of the pump 100 with the flex guide 306 in the non-compressed state 412 (i.e., household battery configuration) with the household batteries 500 installed. The household batteries 500 have a midline 700 that is below the apex 400b of the flex guide 306. The pump additionally includes electronics 702 (e.g., a processor/controller for controlling the pump 100) that are coupled to the electrical contacts 320/322/324 and to a pumping mechanism 704 (e.g., a peristaltic pump) that acts on a tube to pump fluid from a container to a patient. The resilient member 310b is positioned such that its midpoint is positioned between the laterally adjacent household batteries 500c and 500d and a plane normal to the surface of the resilient member 310b extends between the laterally adjacent batteries 500c and 500d.

Figure 7B:
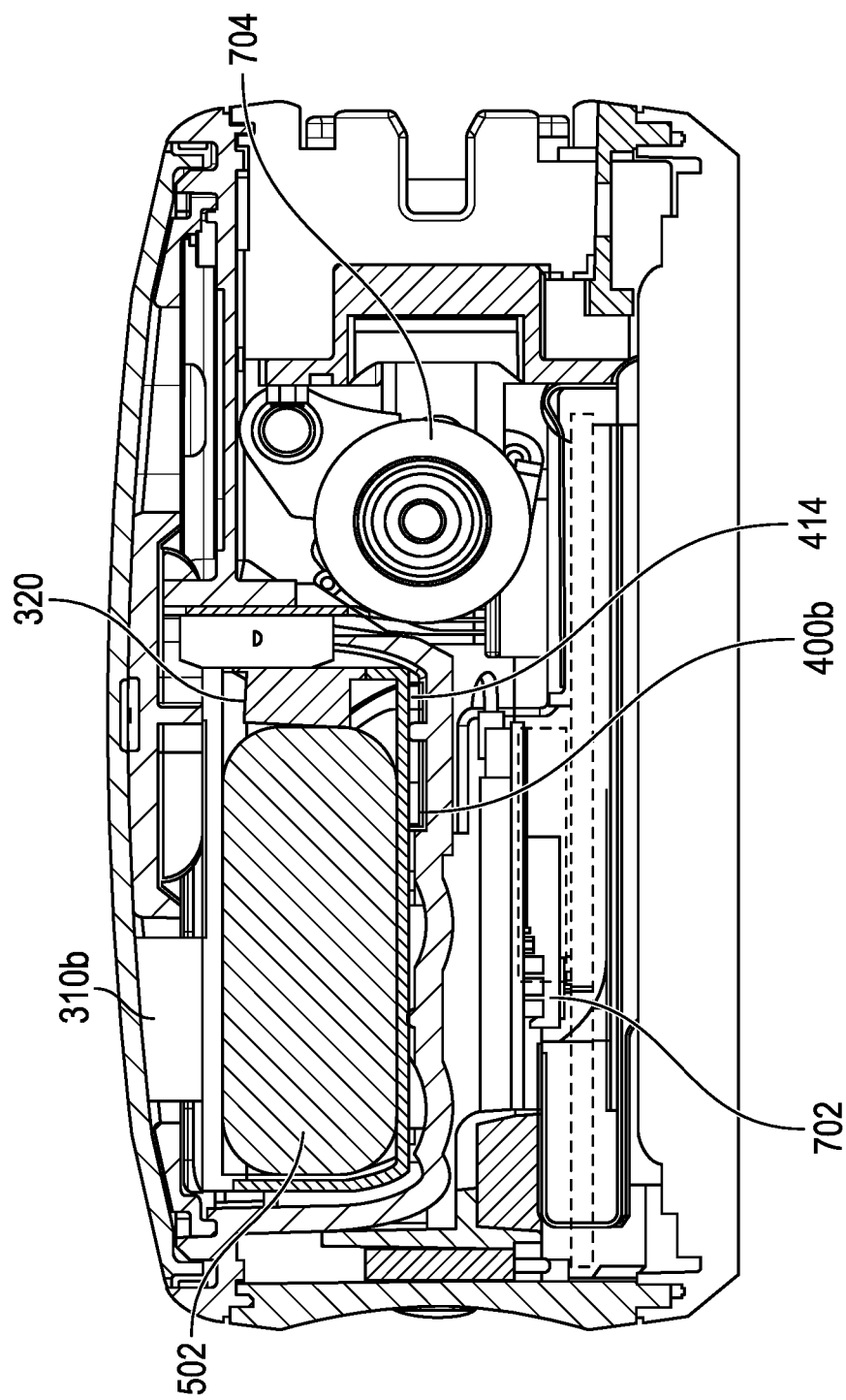
FIG. 7B is a bottom cutaway view of the example ambulatory infusion pump of FIG. 1 in the battery pack configuration with the battery pack installed.

FIG. 7B is a bottom cutaway view of the pump 100 with the flex guide 306 in the compressed state 414 (i.e., battery pack configuration) with the battery pack 502 installed. Compressing the flex guide 306 provides more area for accommodating the battery pack 502 and allows electrical connection of the battery pack 502 to the battery pack connector 320.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An ambulatory pump comprising:
   a pump;
   a controller coupled to the pump for controlling the pump to deliver fluid to a patient;
   a battery compartment electrically coupled to the pump and the controller, the battery compartment defining a cavity for alternately receiving a battery pack and a plurality of household batteries, the cavity having a bottom surface and each of the plurality of household batteries having an insertion depth perpendicular to the bottom surface when received by the cavity; and a flex guide on the bottom surface within the cavity, the flex guide having a compressed state and a non-compressed state, a profile of the flex guide having a height that is greater than half the insertion depth in the non-compressed state and that is less than half the insertion depth in the compressed state.

2. The ambulatory pump of claim 1, wherein the flex guide is positioned within the cavity to be in the compressed state when the battery pack is received.

3. The ambulatory pump of claim 2, wherein the flex guide is positioned within the cavity to be in the non-compressed state with the plurality of household batteries are received and is configured to prevent lateral movement of the plurality of household batteries.

4. The ambulatory pump of claim 3, wherein each of the plurality of household batteries is a cylindrical battery having a radius between 6.5 mm and 7.5 mm and the insertion depth is between 13 mm and 15 mm.

5. The ambulatory pump of claim 3, wherein the cavity is configured to receive at least two household batteries in series and wherein the flex guide includes a first arch configured to engage a first of the at least two household batteries and a second arch configured to engage a second of the at least two household batteries to prevent lateral movement of the at least two household batteries.

6. The ambulatory pump of claim 5, wherein, when the at least two household batteries are received, the first arch contacts the first battery at a first touch zone and at a second touch zone that is spaced from the first touch zone and the second arch contacts the second battery at a third touch zone and at a fourth touch zone that is spaced from the third touch zone.

7. The ambulatory pump of claim 6, wherein the flex guide includes an attachment region positioned between the first arch and the second arch, the attachment region is coupled to the bottom surface of the of the battery compartment, the first arch includes a first edge facing the first battery when installed, the second arch includes a second edge facing the second battery when installed, and the first and second edges travel in a singular plane perpendicular to the bottom surface between the compressed and non-compressed states.

8. The ambulatory pump of claim 7, wherein, the first arch includes a third edge facing away from the first battery when installed, the second arch includes a fourth second edge facing away from the second battery when installed, and the third and fourth edges travel do not travel in a singular plane perpendicular to the bottom surface between the compressed and non-compressed states.

9. The ambulatory pump of claim 1, wherein the at least two household batteries comprise a first pair of batteries in series and a second pair of batteries in series that are adjacent the first pair of batteries in series and wherein the ambulatory pump further comprises:

a housing containing the pump, the controller, the battery compartment, and the flex guide;

an access cover that attaches to the housing, wherein the access cover encloses the cavity when attached to the housing; and a resilient member coupled to the access cover and positioned on the access cover such that, when the access cover is attached to the housing, a plane extending perpendicular from a surface of the resilient member facing the batteries extends between the first and second pairs of batteries.

10. The ambulatory pump of claim 1, wherein the cavity includes a first portion configured to receive the plurality of household batteries and a second portion configured to receive the battery pack, the second portion includes the first portion and the flex guide, and the first portion does not include the flex guide.

11. The ambulatory pump of claim 10, further comprising:

electrical household battery contacts coupled to the controller and positioned within the first portion; and electrical battery pack contacts coupled to the controller and positioned within the second portion outside the first portion.

12. The ambulatory pump of claim 11, wherein the flex guide is positioned within the second portion between the first portion and the electrical battery pack contacts.

13. The ambulatory pump of claim 11, wherein the electrical household battery contacts constrain the plurality of household batteries in a longitudinal direction when installed and constrain the battery pack in the longitudinal direction when installed.

14. The ambulatory pump of claim 13, wherein the electrical household battery contacts are not in electrical contact with the battery pack when installed.

15. A battery compartment for use with an ambulatory pump, the battery compartment comprising:

a cavity for alternately receiving a battery pack and a plurality of household batteries, each of the plurality of household batteries having an insertion depth perpendicular to the bottom surface when received by the cavity; and a flex guide on the bottom surface within the cavity, the flex guide having a compressed state and a non-compressed state, a profile of the flex guide having a height that is greater than half the insertion depth in the non-compressed state and that is less than half the insertion depth in the compressed state.

16. The battery compartment of claim 15, wherein the flex guide is positioned within the cavity to be in the compressed state when the battery pack is received.

17. The battery compartment of claim 16, wherein the flex guide is positioned within the cavity to be in the non-compressed state with the plurality of household batteries are received and is configured to prevent lateral movement of the plurality of household batteries.

18. The battery compartment of claim 17, wherein the cavity is configured to receive at least two household batteries in series and wherein the flex guide includes a first arch configured to engage a first of the at least two household batteries and a second arch configured to engage a second of the at least two household batteries to prevent lateral movement of the at least two household batteries.

19. The battery compartment of claim 18, wherein, when the at least two household batteries are received, the first arch contacts the first battery at a first touch zone and at a second touch zone that is spaced from the first touch zone and the second arch contacts the second battery at a third touch zone and at a fourth touch zone that is spaced from the third touch zone.

20. The battery compartment of claim 15, wherein the cavity includes a first portion configured to receive the plurality of household batteries and a second portion configured to receive the battery pack, the second portion includes the first portion and the flex guide, and the first portion does not include the flex guide; and wherein the battery compartment further comprises:
- electrical household battery contacts positioned within the first portion; and
- electrical battery pack contacts positioned within the second portion outside the first portion;
- wherein the flex guide is positioned within the second portion between the first portion and the electrical battery pack contacts.

* * * * *